United States Patent [19]

Hürner et al.

[11] Patent Number: 5,667,807
[45] Date of Patent: Sep. 16, 1997

[54] THERMAL GRANULATION PROCESS

[75] Inventors: Ingrid Hürner, Düsseldorf; Peter Danz, Köln; Reinhard Walter, Leverkusen, all of Germany; Joachim Maasz, Granger, Ind.; Georg Frank, Wuppertal, Germany

[73] Assignee: Bayer Aktiengesellschaft, Leverkusen, Germany

[21] Appl. No.: 447,674

[22] Filed: May 23, 1995

[30] Foreign Application Priority Data

May 30, 1994 [DE] Germany .................. 44 18 837.4

[51] Int. Cl.$^6$ .................................. A61K 9/14
[52] U.S. Cl. .................. 424/489; 424/466; 424/455; 424/458; 424/474; 424/470
[58] Field of Search ................. 424/489, 488, 424/490, 499, 498

[56] References Cited

U.S. PATENT DOCUMENTS

| | | | |
|---|---|---|---|
| 4,937,080 | 6/1990 | Appelgren et al. | 424/490 |
| 5,169,645 | 12/1992 | Shukla et al. | 424/499 |
| 5,403,593 | 4/1995 | Royce | 424/489 |

FOREIGN PATENT DOCUMENTS

| | | |
|---|---|---|
| 0362728 | 11/1994 | European Pat. Off. . |
| 3833448 | 4/1990 | Germany . |
| 4031881 | 4/1992 | Germany . |
| 9206679 | 4/1992 | WIPO . |

OTHER PUBLICATIONS

Jim McCabe ("Twin Screw Extrusion in the Production of Novel Dosage Forms"), Pharmaceutical Manufacturing Review, 1994.

*Primary Examiner*—Thurman K. Page
*Assistant Examiner*—William E. Benston, Jr.
*Attorney, Agent, or Firm*—Sprung Horn Kramer & Woods

[57] ABSTRACT

The invention relates to a thermal process for the production of directly tablettable granules and pharmaceutical preparations produced therefrom.

8 Claims, No Drawings

THERMAL GRANULATION PROCESS

The invention relates to a thermal process for the production of directly tablettable granules and a pharmaceutical preparation produced therefrom.

Direct tabletting processes are preferred for the industrial production of tablets. Direct tabletting means that the constituents of a tablet are pressed directly without preceding granulation processes. As a result time- and cost-consuming process steps, such as e.g. solvent removal and drying after a moist granulation, are unnecessary.

High demands with respect to flowability, density, particle size etc. of their starting substances are made, however, on powder mixtures which are to be directly tabletted in order to guarantee a uniform, homogeneous supply of the powder to the tablet and thus batch homogeneity. Many active compounds, such as e.g. ibuprofen and ketoprofen are unsuitable for direct tabletting due to their unfavourable physicochemical properties.

For low-melting active compounds, i.e. for active compounds having a melting point of between 30 and 200° C., preferably between 40 and 150° C., a process has now been found to process the active compound directly to give directly tablettable granules in a simple manner together with the desired customary auxiliaries.

Processes are already known from the prior art according to which tabletting material is thermally treated as a preparation for direct tabletting. German Offenlegungsschrift DE 3 833 448 describes a process for the production of ibuprofen preparations by direct tabletting. According to this process, the active compound is completely melted in a melting apparatus and then solidified and crystallized on a contact cooling apparatus. The resulting flakes of active compound are ground to give a powder having improved flow properties. This ibuprofen powder can be mixed with suitable auxiliaries and then directly tabletted.

EP-A 305 356 describes granules which are formed by melt granulation of a low-melting substance with its own melt. As a result of the melt coating on the crystalline substance, the physicochemical properties, in particular the flow properties, are changed positively, which leads to easier tabletting.

Using the processes known hitherto, only individual (active) compounds are prepared for direct tabletting, the other constituents of the pharmaceutical forms still having to be admixed. Depending on the nature and amount of these admixtures, the abovementioned powder technology problems which prevent or adversely affect direct tabletting can again occur.

A further advantage of the process according to the invention lies in the fact that especially with relatively high-dose active compounds such as, for example, ibuprofen only a small amount of auxiliaries has to be added. This leads to small pharmaceutical forms which are particularly pleasant for the consumer to take.

The invention relates to a thermal process for the production of directly tablettable granules, containing an active compound having a low melting point and at the same time the necessary tablet auxiliaries, which is characterized in that a mixture of active compound and the necessary auxiliaries is processed by means of a melt extrusion at elevated temperature to give a homogeneous non-agglutinating extrudate which is then comminuted to give tablettable granules.

The invention also relates to granules and extrudates prepared in this way and their use in the production of tablets.

In the production of these granules or extrudates, the active compounds having a low melting point employed fulfil the function of a binder or of a solid solvent. The granules thus obtained preferably contain 25 to 95% by weight, preferably 35 to 90% by weight, of low-melting constituents comprising active compound and auxiliaries. Low-melting active compounds which may be mentioned are preferably active substances having a melting point of between 30 and 200° C., in particular of between 40 and 150° C. These include, in particular, non-steroidal analgesic substances and antiinflammatory substances of the arylpropionic acid type. The active compounds ibuprofen, ketoprofen, naproxen and indomethacin in the form of their racemates and also as enantiomers are of particular interest.

Auxiliaries which may be mentioned are the customary tablet auxiliaries such as binders, fillers, disintegrants etc. The granules prepared according to the invention are suitable for the production of pharmaceutical preparations such as tablets, effervescent tablets, capsules, inspissated juices and dry suspensions.

Production is carried out by mixing the low-melting active compound with the suitable auxiliaries in a mixer and adding this mixture directly to a heatable extruder. By means of the mixing and kneading elements of the extruder, the mixture is compacted to give an extrudate at a temperature at which a part of the active compound is melted. This extrudate is pressed through a perforated plate to give thin strands of 0.3–2.0 mm diameter and comminuted after cooling to the desired particle size of the granules. The granules thus obtained can immediately be subjected to tabletting, only a lubricant, being required. By means of this process according to the invention, apart from the lubricant all auxiliaries such as binder, disintegration auxiliaries, fillers and other auxiliaries can be incorporated directly into the granules. As a result tedious reprocessing processes become unnecessary. Since time-consuming and environmentally polluting granulation and drying processes are likewise unnecessary, the process according to the invention is distinguished by high cost efficiency. Surprisingly, in addition to their good tabletting ability, the ibuprofen tablets prepared according to the invention are also distinguished by an outstanding release of the active compound as can be seen from FIG. 1. Suitable auxiliaries which may be mentioned which can be incorporated into the granules directly by the process according to the invention are: microcrystalline and microfine cellulose (Avicel and Elcema types), starch and modified starches such as rice starch or maize starch, highly disperse silica such as Aerosil, polyvinylpyrrolidones and calcium salts such as e.g. calcium mono-, di- or triphosphates or calcium carbonate, as fillers, sugar alcohols such as mannitol, xylitol or sorbitol), and, as active disintegrants, crosslinked starches, crosslinked cellulose and crosslinked polyvinylpyrrolidone, and other substances customary for tabletting.

EXEMPLARY EMBODIMENTS

Example 1

|    | Substance          | Mass [g] |
|----|--------------------|----------|
| 1. | (R,S)-Ibuprofen    | 2000     |
| 2. | Avicel             | 430      |
| 3. | Aerosil            | 100      |
| 4. | Maize starch       | 390      |
| 5. | Ac-Di-Sol          | 60       |
| 6. | Magnesium stearate | 20       |

The substances 1 to 5 are mixed in a tumble mixer and then added to a heatable twin screw extruder.

The extrusion temperature is 67° C.

Homogeneous, non-agglutinating strands cooling in the air emerge from the die plate. These are then forcibly sieved through a 0.8 mm Frewitt sieve such that granules having a particle size between 0.05 and 0.8 mm are formed. The granules are mixed with the lubricant magnesium stearate in a tumbler mixer and then directly pressed in a suitable tablet press to give tablets of 300 mg.

Example 2

|   | Substance | Mass [g] |
|---|-----------|----------|
| 1. | (R,S)-Ibuprofen | 2000 |
| 2. | Avicel | 430 |
| 3. | Aerosil | 100 |
| 4. | Maize starch | 450 |
| 5. | Magnesium stearate | 20 |

The extrusion of the substances 1 to 4 is carried out analogously to Example 1 and the extrusion temperature is likewise 67° C.

Further processing of the extrudate to give tablets having a weight of 300 mg is carried out as in Example 1.

Example 3

|   | Substance | Mass [g] |
|---|-----------|----------|
| 1. | (S)-Ibuprofen | 2000 |
| 2. | Avicel | 430 |
| 3. | Aerosil | 100 |
| 4. | Maize starch | 390 |
| 5. | Ac-Di-Sol | 60 |
| 6. | Magnesium stearate | 20 |

1, 2, 3 and 5 are mixed in a tumbler mixer and extruded as in Example 1.

The extrusion temperature is about 48° C.

After sieving through the Frewitt 0.8 mm sieve, the granules are first mixed with 4 and the lubricant 6 is then added and mixed.

The granules are likewise pressed to give tablets of 300 mg.

Example 4

|   | Substance | Mass [g] |
|---|-----------|----------|
| 1. | (R,S)-Ketoprofen | 500 |
| 2. | Avicel | 500 |
| 3. | Maize starch | 480 |
| 4. | Magnesium stearate | 20 |

1, 2 and 3 are mixed and extruded as indicated in Example 1, and the comminuted extrudate is mixed with the lubricant and pressed to give tablets having an intended weight of 150 mg.

The extrusion temperature is 86° C.

We claim:

1. Process for the production of directly tablettable granules containing an active compound having a melting point between 40° and 150° C. and tablet auxiliaries, which comprises forming a mixture of said active compound and said auxiliaries, heating said mixture to a temperature of from 40° to 200° C. in a melt extruder to melt a part of said active compound and form a mixture of said active compound and said auxiliaries wherein a part of said active compound is in the form of a melt, and extruding said mixture in which said active compound is present partly in the form of a melt, to produce a homogeneous non-agglutinating extrudate, and then comminuting said extrudate to form granules.

2. Process according to claim 1, characterized in that, as active compound, non-steroidal analgesic active compounds and/or antiinflammatory substances of the arylpropionic acid type are employed.

3. Process according to claim 1, characterized in that, as active compound, ibuprofen, ketoprofen, naproxen or indomethacin are employed as racemates or in their enantiomerically pure form.

4. Process according to claim 1, wherein the mixture from the extruder is pressed through a perforated plate to give thin strands of 0.3 to 2.0 mm diameter and these are comminuted after cooling to give granules.

5. Granules produced by the process of claim 1.

6. Process for the production of tablets, which comprises directly tabletting granules according to claim 5.

7. Tablets produced by the process of claim 6.

8. The process of claim 3, wherein said active compound is ketoprofen or ibuprofen.

* * * * *